United States Patent [19]

Ueda et al.

[11] Patent Number: 4,874,869
[45] Date of Patent: * Oct. 17, 1989

[54] HYDANTOIN DERIVATIVES AND MEDICINES CONTAINING THE SAME

[75] Inventors: Kouichiro Ueda, Saitama; Satoru Tanaka, Tokyo; Toshinobu Kunii; Kengo Kagei, both of Gifu; Tadashi Sato; Hideki Ono, both of Aichi; Issei Ohtsuka; Mayumi Kawase, both of Gifu; Toshiharu Ohgoh, Aichi; Tsuneo Wakabayashi, Gifu, all of Japan

[73] Assignee: Eisai Co., Ltd., Tokyo, Japan

[*] Notice: The portion of the term of this patent subsequent to Sep. 10, 2002 has been disclaimed.

[21] Appl. No.: 73,915

[22] Filed: Jul. 13, 1987

Related U.S. Application Data

[60] Continuation of Ser. No. 815,309, Dec. 31, 1985, abandoned, which is a continuation of Ser. No. 688,146, Dec. 31, 1984, abandoned, which is a division of Ser. No. 500,801, Jun. 7, 1983, Pat. No. 4,540,704, which is a continuation of Ser. No. 284,566, Jul. 17, 1981, abandoned.

[30] Foreign Application Priority Data

Jul. 21, 1980 [JP] Japan ................................ 60-98695

[51] Int. Cl.$^4$ .......................................... C07D 491/10
[52] U.S. Cl. .................................................. 548/309
[58] Field of Search ......................... 548/309; 514/389

[56] References Cited

U.S. PATENT DOCUMENTS 4,117,230 9/1978 Sarges .................................. 548/309

FOREIGN PATENT DOCUMENTS 2455046 11/1980 France .............................. 548/309

Primary Examiner—Mary C. Lee
Assistant Examiner—Zinna Northington
Attorney, Agent, or Firm—Wenderoth, Lind & Ponack

[57] ABSTRACT

Novel hydantoin derivatives and salts thereof, the process for the preparation thereof, and medicines containing the same, wherein the hydantoin derivatives are represented by the general formula:

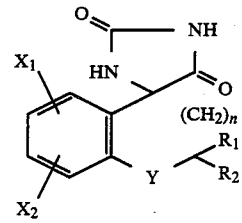

wherein $X_1$ and $X_2$, which may be the same or different, mean independently hydrogen atom, a halogen atom, a lower alkyl group or a lower alkoxy group; Y means oxygen atom or sulfur atom, $R_1$ and $R_2$, which may be the same or different, mean independently hydrogen atom, a lower alkyl group or phenyl group, or the both may form a ring with a carbon atom which is combined with them, excluding the case wherein both $R_1$ and $R_2$ are hydrogen atom at the same time, and n means an integer of 0 or 1. The novel hydantoin derivatives and salts thereof have excellent effects for the treatment of the complications of the diabetes mellitus.

1 Claim, 1 Drawing Sheet

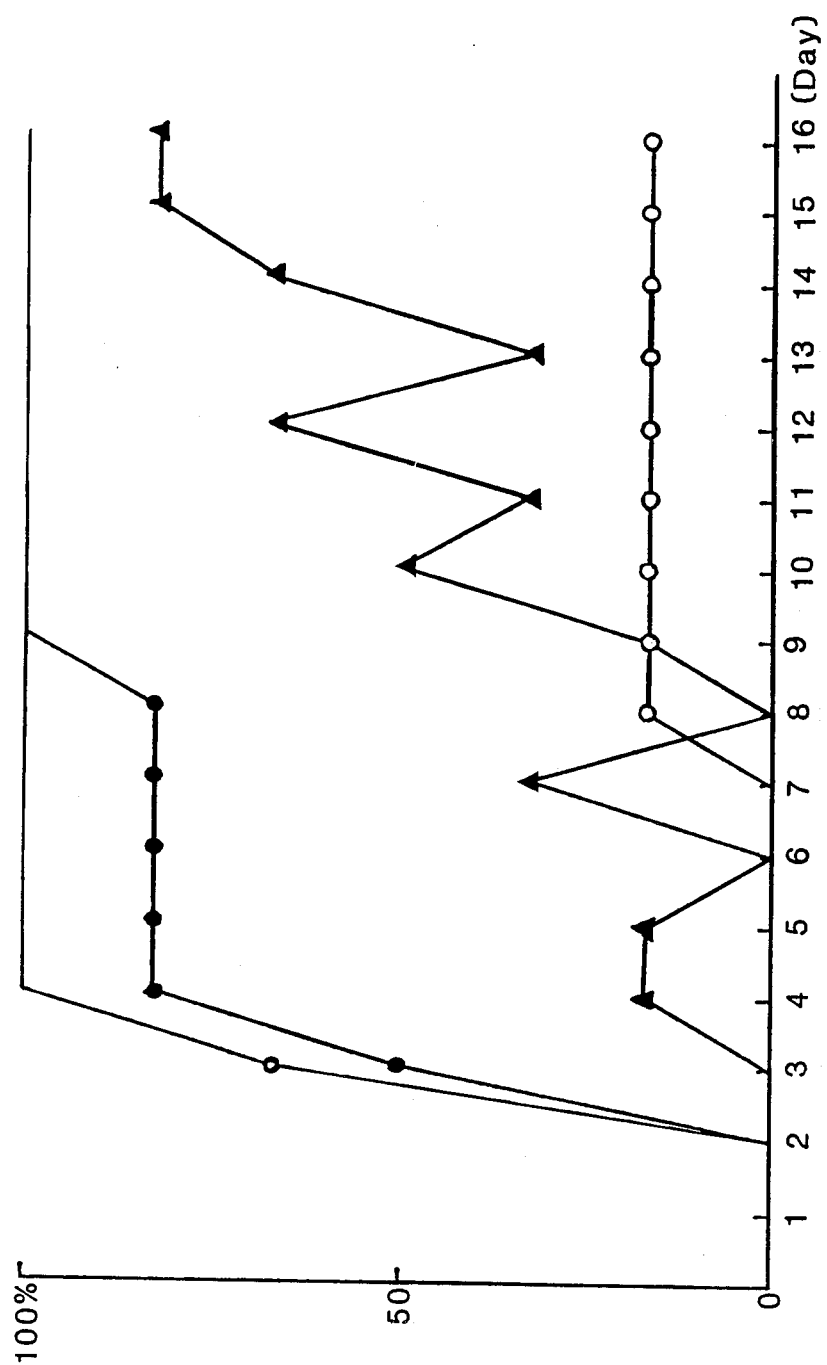

HYDANTOIN DERIVATIVES AND MEDICINES CONTAINING THE SAME

This application is a continuation of now abandoned application Ser. No. 815,309, filed Dec. 31, 1985, which is a continuation of now abandoned application Ser. No. 688,146, file of Dec. 31, 1984, which is a Rule 60 Division of Ser. No. 500,801, filed June 7, 1983, now U.S. Pat. No. 4,540,704, which is a Rule 62 Continuation of Ser. No. 284,566 filed July 17, 1981, now abandoned.

This invention relates to novel hydantoin derivatives having excellent pharmaceutical properties and to compositions containing the same. More particularly, the invention relates to the hydantoin derivatives represented by the general formula:

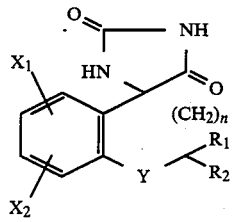

[I]

wherein $X_1$ and $X_2$, which may be the same or different, independently represent a hydrogen atom, a halogen atom, a lower alkyl group or a lower alkoxy gorup, Y represents an oxygen atom or sulfur atom, $R_1$ and $R_2$, which may be the same or different, independently represent a hydrogen atom, a lower alkyl group or phenyl group, or the both may form a ring with carbon atoms which are combined with them, excluding the case wherein both $R_1$ and $R_2$ are hydrogen atoms, and n represents an integer of 0 or 1, and salts thereof an pharmaceutical compositions containing the same.

In the general formula [I], the lower alkyl or alkoxy groups as set forth in the definitions of $X_1$, $X_2$, $R_1$ and $R_2$ mean an alkyl group of straight or branched chain, containing 1-6 carbon atoms, for example, an alkyl group such as methyl, ethyl, n-propyl, isopropyl, n-butyl, isobutyl, tert-butyl, n-pentyl, isoamyl, n-hexyl or the like, or an alkoxy group on the basis of such alkyl groups. The halogen atom as set forth in the definition of $X_1$ and $X_2$ means, from a practical standpoint, chlorine, bromine, iodine or fluorine. The ring as set forth in the definition of $R_1$ and $R_2$, which is formed by the both and carbon atoms combined with them means, from a practical standpoint, for example, a group such as cyclobutyl, cyclopentyl, cyclohexyl or the like.

In the present invention, the salts mean pharmaceutically acceptable salts and, from a practical standpoint, the salts of a cation, such as sodium, potassium, calcium, magnesium or the like.

It is assumed that a compound according to the invention may exist in a form of two stereoisomers and the respective optical isomers thereof, since it contains one or two asymmetric carbon atoms on their structure. This invention, of course, includes any of such isomers.

The hydantoin derivatives provided by this invention are all novel compounds which have not been reported in the literature, and which have excellent effects in the treatment and prevention of the various chronic symptoms accompanying with the diabetes mellitus, that is, the complications of diabetes mellitus, for example, diabetic cataracts, diabetic neuropathy, fine blood-vessel lesions such as diabetic nephrosis and the like, diabetic retinopathy, and various arteriosclerotic blood-vessel lesions originating from diabetes mellitus.

Heretofore, there have been commercially available a number of antidiabetic drugs, such as those based on sulfonium urea, mesoxalates, guanidine derivatives or the like. These, however, are not medicine for the direct treatment of the diabetes mellitus, but a symptomatic medicine for the hyperglycemia.

It is fair to say, that there are few medicines for the treatment of various chronic symptoms and complications accompanying diabetes mellitus, for example, diabetic cataracts, diabetic neuropathy, diabetic retinopathy and the like, and that there is no effective method for the treatment thereof. Particularly, there is essentially no medical treatment for cataracts which is a white turbidity of the crystalline lens.

Over a long period of time, a number of studies have been conducted to find effective medicines for such incurable diseases, but no successful ones have yet been found.

One of the objectives of such studies was to find an Aldose reductase inhibitor. In "Science", 182, 1146-8 (1973), J. H. Kinoshita et al. reported their theory that, in a patient suffering from the diabetes mellitus, the activity of the Aldose reductase in the crystalline lens in the eyes increases, sugars such as glucose and the like are introduced therein, and the sugars are reduced by enzymes into polyols such as sorbitol and the like, resulting in the accumulation of these polyols which are the main cause of stroma lesions of the crystalline lens, etc. Since then, the search for an Aldose reductase inhibitor based on the theory of J. H. Kinoshita has been extensively conducted.

Thus, Reinhard Sarges has found that particular hydantoin derivatives exhibit Aldose reductase inhibition (Japanese Patent Application Laid-open No. 53653/78) etc., and among these derivatives, d-6-fluorospiro-[chromane-4,4'-imidazolidine]-2'5'-dione (general name "Sorbinil⇌") has been proposed.

We, also, have been engaged over a long period of time in studying numerous and varied compounds for the purpose of developing a remedy for such complications accompanying diabetic mellitus. In spite of these great difficulties, we have found at last that hydantoin derivatives represented by the following general formula:

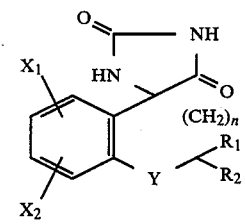

[I]

wherein $X_1$ and $X_2$, which may be the same or different, independently represent a hydrogen atom, a halogen atom, a lower alkyl group or a lower alkoxy group, Y represents oxygen atom or sulfur atom, $R_1$ and $R_2$, which may be the same or different, independently represent a hydrogen atom, a lower alkyl group or phenyl group, or they form a ring with a carbon atoms combined with them, excluding the case wherein the both $R_1$ and $R_2$ are hydrogen atom, and n represents an integer of 0 or 1, are very effective for the treatment of said incurable diseases.

The group of the compounds provided by this invention exhibits not only strong Aldose reductase inhibition activity but, surprisingly strong activity in vivo, which is worthy of special mention. Moreover, the toxicity of the group of the compounds provided by this invention is extremely weak, as is and also other functions such as the central function and the effect on the central nervous system and the like. This means that an extremely small dose is clinically acceptable, and is very important, in view of the fact that the continuous administration is necessarily required for the treatment of diabetic cataracts, diabetic neuropathy, diabetic retinopathy, fine blood vessel lesions such as diabetic nephrosis and the like, as well as complications such as various arteriosclerotic blood-vessel lesions originating from diabetes mellitus.

The compounds according to this invention are extremely valuable because there is essentially no remedy drug for such incurable diseases in the present time.

Therefore, an object of this invention is to provide novel compounds effective for chronic symptoms and complications accompanying diabetes mellitus, for example, diabetic cataracts, diabetic neuropathy, the diabetic retinopathy, fine blood-vessel lesions such as the diabetic nephrosis and the like, and various arteriosclerotic blood-vessel lesions originating from the diabetes mellitus.

Another object of this invention is to provide a process for the preparation of a novel compound effective for various chronic symptoms and complications accompanying diabetes mellitus, for example, diabetic cataracts, diabetic neuropathy, fine blood-vessel lesions such as diabetic nephrosis and the like, various arteriosclerotic blood-vessel lesion originating from the diabetes mellitus and diabetic retinopathy.

The compounds according to this invention can be prepared by varous processes. A typical process is exemplified as follows:

The compound according to this invention is prepared by condensation of three ingredients of (1) a compound represented by the formula [II]:

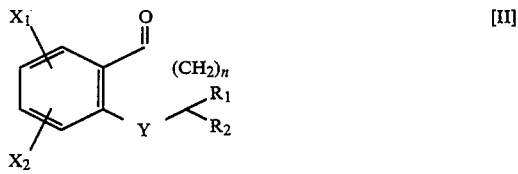

wherein $X_1$, $X_2$, $R_1$, $R_2$, Y and n have the same meanings as defined above, (2) an alkali metal cyanide such as sodium cyanide, potassium cyanide, and (3) ammonium carbonate.

The examples of preferred solvents used in the reaction according to this invention include lower alkanoamides such as acetylamide, water miscible alkanols such as methanol, ethanol, and propanol, and cyclic ethers such as dioxane and tetrahydrofuran, lower alkylene glycols such as ethylene glycol and trimethylene glycol, and N,N-dialkylamides such as N,N-dimethylformamide and N,N-diethylformamide, etc.

Although the reaction according to this invention depends on the starting material represented by the above formula [II], the reaction is carried out preferably at a temperature of 50°–150° C. for the period of time from about 4 hours to about 4 days.

In the reaction according to this invention, the preferred proportions of the above starting materials (1), (2) and (3) is such that the alkali metal cyanide (2) and the ammonium carbonate (3) are used in an equivalent amount at least slightly in excess of the compound (1). After completion of the reaction, the subject material [I] according to this invention is isolated in the form of a readily recoverable precipitate by a conventional method, for example, by diluting the reaction mixture with water at first, and cooling the produced aqueous solution to the room temperature, then acidifying it.

When the subject material [I] is a 2-mono substituted derivative, it is expected to form two stereoisomers based on two asymmetric carbon atoms contained therein.

However, according to the process of this invention, one of the isomers is predominantly produced. The said isomer has higher activities such as the inhibition of sorbitol accumulation as described later than the other isomer which is produced in very small ratio. The process according to this invention can be therefore referred as a very preferable process.

In this process, the starting material of the general formula [II] may be prepared by various processes. The materials prepared by any processes can be, of course, used in this invention.

For example, the compound, 6-fluoro-2-methyl-4-chromanone of the formula [II] wherein $X_1$=H, $X_2$=6-F, $R_1$=H, $R_2$=CH$_3$, n=1, Y=0, can be produced by condensing p-fluorophenol with crotonic acid in the presence of polyphosphoric acid to form a closed ring. The compound, 6-chloro-2-spiro-cyclohexan-4-chromanone of the formula [II] wherein $X_1$=H, $X_2$=6-Cl, n=1, Y=0, and both $R_1$ and $R_2$ form a cyclohexane ring, is produced by condensing 2-hydroxy-5-chloroacetophenone with cyclohexanone in the presence of pyrrolidine and the like, to form a closed ring.

The compound, 5-chloro-2,2-dimethyl-3-benzofuranone of the formula [II] wherein $X_1$=H, $X_2$=5-Cl, n=0, Y=0, $R_1$=$R_2$=CH$_3$, is synthesized, for example, according to the reaction equation as follows:

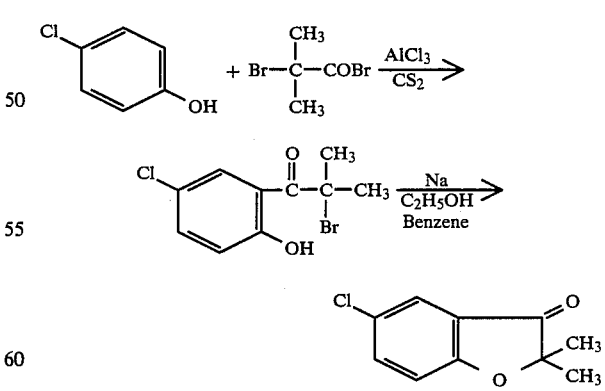

The compound, 5-chloro-2-methyl-3-benzofuranone of the formula [II] wherein $X_1$=H, $X_2$=5-Cl, n=0, Y=0, $R_1$=H, $R_2$=CH$_3$, is produced by the similar procedure as described above in the production of 5-chloro-2,2-dimethyl-3-benzofuranone, for example, according to the following reaction equation:

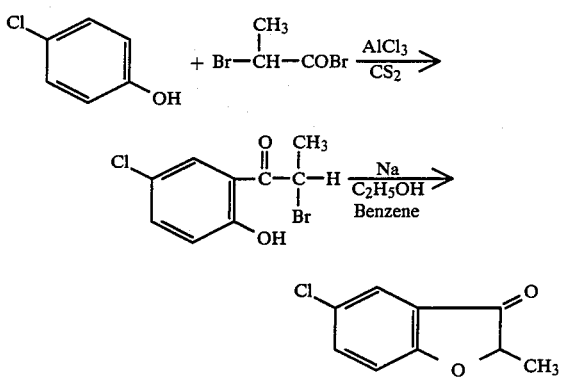

The compound, 6-chloro-2-methyl-4-thiochromanone of the general formula [II] wherein $X_1=H$, $X_2=6\text{-}Cl$, $n=1$, $Y=S$, $R_1=H$, $R_2=CH_3$, is produced by condensing p-chlorothiophenol with crotonic acid in the presence of polyphosphoric acid to form a closed ring.

The compound, 6-chloro-2-phenyl-4-chromanone of the formula [II] wherein $X_1=H$, $X_2=6\text{-}Cl$, $n=1$, $Y=O$, $R_1=H$, $R_2=$phenyl group, is synthesized, for example, according to the reaction equation as follows:

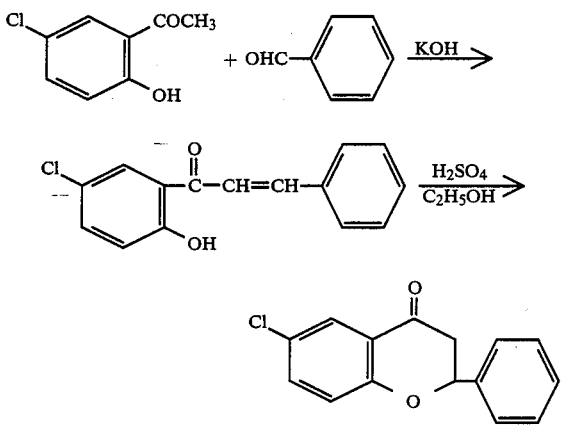

Illustrative of the compounds according to this invention include:
6-Fluoro-2-methyl-spiro-[chroman-4,4'-imidazolidine]-2',5'-dione
6-Chloro-2-methyl-spiro-[chroman-4,4'-imidazolidine]-2',5'-dione
6-Chloro-2,2-dimethyl-spiro-[chroman-4,4'-imidazolidine]-2',5'-dione
6-Fluoro-2,2-dimethyl-spiro-[chroman-4,4'-imidazolidine]-2',5'-dione
5-Chloro-2,2-dimethyl-spiro-[benzofuran-3,4'-imidazolidine]-2',5'-dione
5-Fluoro-2,2-dimethyl-spiro-[benzofuran-3,4'-imidazolidine]-2',5'-dione
5-Chloro-2-methyl-spiro-[benzofuran-3,4'-imidazolidine]-2',5'-dione
5-Fluoro-2-methyl-spiro-[benzofuran-3,4'-imidazolidine]-2',5'-dione
6-Methyl-2,2-dimethyl-spiro-[chroman-4,4'-imidazolidine]-2',5'-dione
6-Methoxy-2,2-dimethyl-spiro-[chroman-4,4'-imidazolidine]-2',5'-dione
6,8-Dichloro-2,2-dimethyl-spiro-[chroman-4,4'-imidazolidine]-2',5'-dione
6-Bromo-2,2-dimethyl-spiro-[chroman-4,4'-imidazolidine]-2',5'-dione
6-Fluoro-2,2-diethyl-spiro-[chroman-4,4'-imidazolidine]-2',5'-dione
6-Chloro-2-ethyl-spiro-[chroman-4,4'-imidazolidine]-2',5'-dione
6-Chloro-2-n-propyl-spiro-[chroman-4,4'-imidazolidine]-2',5'-dione
6-Fluoro-2-ethyl-spiro-[chroman-4,4'-imidazolidine]-2',5'-dione
6-Fluoro-2-n-propyl-spiro-[chroman-4,4'-imidazolidine]-2',5'-dione
6-Chloro-2-isobutyl-spiro-[chroman-4,4'-imidazolidine]-2',5'-dione
6-Chloro-2-isopropyl-spiro-[chroman-4,4'-imidazolidine]-2',5'-dione
6-Chloro-2-n-butyl-spiro-[chroman-4,4'-imidazolidine]-2',5'-dione
6-Methoxy-2-methyl-spiro-[chroman-4,4'-imidazolidine]-2',5'-dione
7-Chloro-2-methyl-spiro-[chroman-4,4'-imidazolidine]-2',5'-dione
6-Methyl-2-methyl-spiro-[chroman-4,4'-imidazolidine]-2',5'-dione
6,7-Dichloro-2-methyl-spiro-[chroman-4,4'-imidazolidine]-2',5'-dione
2,2-Dimethyl-spiro-[chroman-4,4'-imidazolidine]-2',5'-dione
2-Methyl-spiro-[chroman-4,4'-imidazolidine]-2',5'-dione
2,2-Dimethyl-spiro-[thiochroman-4,4'-imidazolidine]-2',5'-dione
6-Chloro-2-phenyl-spiro-[chroman-4,4'-imidazolidine]-2',5'-dione
6-Fluoro-2-methyl-spiro-[thiochroman-4,4'-imidazolidine]-2',5'-dione
6-Fluoro-2,2-dimethyl-spiro-[thiochroman-4,4'-imidazolidine]-2',5'-dione
6-Chloro-2-methyl-spiro-[thiochroman-4,4'-imidazolidine]-2',5'-dione
6-Chloro-2,2-dimethyl-spiro-[thiochroman-4,4'-imidazolidine]-2',5'-dione
6-Fluoro-2,2-diethyl-spiro-[thiochroman-4,4'-imidazolidine]-2',5'-dione
6,8-Dichloro-2,2-dimethyl-spiro-[thiochroman-4,4'-imidazolidine]-2',5'-dione
6-Fluoro-2-n-pentyl-spiro-[chroman-4,4'-imidazolidine]-2',5'-dione
6-Chloro-2-n-hexyl-spiro-[chroman-4,4'-imidazolidine]-2',5'-dione
Cyclohexane<spiro-2>-6-methyl-spiro-[chroman-4,4'-imidazolidine]-2',5'-dione
Cyclohexane<spiro-2>-6-chloro-spiro-[chroman-4,4'-imidazolidine]-2',5'-dione
Cyclopentane<spiro-2>-6-chloro-spiro-[chroman-4,4'-imidazolidine]-2',5'-dione
Cyclopentane<spiro-2>-6-methoxy-spiro-[chroman-4,4'-imidazolidine]-2',5'-dione, and
Cyclopentane<spiro-2>-6-methyl-spiro-[chroman-4,4'-imidazolidine]-2',5'-dione The compounds provided by this invention are useful for the treatment and the prevention of various chronic symptoms and effects of diabetes mellitus and diabetic complications thereof, such as, for example, diabetic cataracts, diabetic neuropathy, diabetic retinopathy, various arteriosclerotic blood-vessel lesions originating from diabetes mellitus, and fine blood-vessel lesions such as diabetic nephritis etc., and hence, this invention is very valuable. The effects of the compounds of this invention will be explained in more detail.

As is apparent from Experiment 1 below, the compounds according to this invention give fairly high reduction and inhibition of sorbitol accumulation in the lens and the sciatic nerve of diabetic rats. As a control, a typical compound, 6-fluoro-spiro-[chroman-4,4′-imidazolidine]-2′,5′-dione as described in Japanese Patent Application Laid-open No. 53653/78 was selected. As shown in the following Experiments, the compounds according to this invention have an extremely superior effect on the inhibition of sorbitol accumulation, as compared with the control compound. As shown in the following Table 1, 6-fluoro-2-methyl-spiro-[chroman-4,4′-imidazolidine]-2′,5′-dione and 6-chloro-2-methyl-spiro-[chroman-4,4′-imidazolidine]-2′,5′-dione exhibit a superior effect on the inhibition of sorbitol accumulation, to the extent of about 2–10 times, in comparison with the control compound. In detail, the compounds according to this invention are considered to intensely act on the nervous system, since the comopounds according to the invention exhibit very superior inhibition of sorbitol accumulation in, among other, the sciatic nerve. This is particularly advantageous in neuropathy which is one of the incurable complications of diabetes mellitus.

The very superior effect of the compound according to this invention on the inhibition of sorbitol accumulation means that the effect is achieved by even a small dose. This is very important matter, because the continous administration is required in order to treat incurable complications of diabetes mellitus such as diabetic cataracts, the diabetic neuropathy and the like.

This is also similar to the case of Experiment 2 described later, with regard to the cataract formation in galactosemic rats. The compounds according to this invention remarkably delay the formation of cataract in galactosemic rats and reduce or considerably inhibit the accumulation of galactitol in the lens and the sciatic nerve. As is apparent from Experiment 2, the compounds according to this invention show a very low percentage in appearance of cataracts, and superior inhibition of galactitol accumulation, to the extent of above five times, as compared with the control compound.

As is apparent from Example 3 described later, the compounds according to this invention also exhibit very superior inhibition of aldose reductase.

Moreover, it has been found that the compounds provided by this invention have a relatively weak antimetrazol action which is one of the indices of the action on the central nervous system, as compared with the control compound. Thus, those compounds have very great clinical merits because of few side effects, due to a weaker action on the central nervous system.

As described above, continuous administration over long period of time is required depending on the nature of the symptoms or complications to be treated. Therefore, the compounds according to this invention also have a high value in this respect.

The excellent pharmacological action of the compounds according to this invention are illustrated from a practical standpoint by the following Experiments with respect to typical compounds of this invention.

EXPERIMENT 1

Determination of the ability to reduce or inhibit sorbitol accumulation in the lens and the sciatic nerve of streptozotocin-induced diabetic rats The compounds listed in Tables 1 and 2 were tested for the ability to reduce or inhibit the accumulation of sorbitol in the lens and the sciatic nerve of streptozotocin-induced diabetic rats by the method of M. J. Peterson et al., [Metabolism, Vol. 28, No. 4, Supply. 1 (April), 456–461 (1979)]. There was selected, as the control, 6-fluoro-spiro-[chroman-4,4′-imidazolidine]-2′,5′-dione, a typical compound described in the aforesaid Japanese Patent Application laid-open No. 53653/78. In this experiment, the amount of sorbitol accumulation in the lens and the sciatic nerve of the rat was measured 28 hours after induction of diabetes.

The compounds listed in Tables 1 and 2 were orally administered at, the dose levels indicated in the Tables, 4, 8 and 25 hours after the administration of the streptozotocin. The Table 1 shows the experiments conducted at dose levels of 0.2 mg/kg, 1 mg/kg and 5 mg/kg, and the Table 2 shows the experiment conducted at dose levels of 10 mg/kg. The results are shown in Tables 1 and 2, in term of inhibition of sorbitol accumulation (%) afforded by the test compounds, as compared with the case where no compound was administered.

Among the compounds in Tables 1 and 2, the compounds, 6-fluoro-2-methyl-spiro-[chroman-4,4′-imidazolidine]-2′,5′-dione and 6-chloro-2-methyl-spiro-[chroman-4,4′-imidazolidine]-2′,5′-dione represent the respective compounds which are predominantly produced in Examples 1 and 2 described later, these compounds being crystallized materials having melting points of 233°–235° C. and 283°–285° C., respectively.

TABLE 1

|  | Compound | Inhibition of sorbitol accumulation (%) | | | | | |
|---|---|---|---|---|---|---|---|
|  |  | 0.2 (mg/kg) | | 1 (mg/kg) | | 5 (mg/kg) | |
|  |  | lens | Sciatic nerve | lens | Sciatic nerve | lens | Sciatic nerve |
| Control compound | 6-Fluoro-spiro-[chroman-4,4′-imidazolidine]-2′,5′-dione | −29 | 26 | 41 | 15 | 62 | 67 |
|  | 6-Fluoro-2-methyl-spiro-[chroman-4,4′-imidazolidine]2′,5′-dione | 43 | 39 | 80 | 100 | 93 | 100 |
|  | 6-Chloro-2-methyl-spiro-[chroman-4,4′-imidazolidine]-2′,5′-dione | 32 | 73 | 78 | 100 | 93 | 100 |
|  | 6-Chloro-2,2-dimethyl-spiro-[chroman-4,4′-imidazolidine]-2′,5′-dione | 11 | 47 | 60 | 86 | 78 | 95 |
| Compound according to this invention | 6-Fluoro-2,2-dimethyl-spiro-[chroman-4,4′-imidazolidine]-2′,5′-dione | 35 | 22 | 58 | 33 | 72 | 81 |
|  | 7-Chloro-2-methyl-spiro-[chroman- | — | — | — | — | 83 | — |

TABLE 1-continued

| | Inhibition of sorbitol accumulation (%) | | | | | |
|---|---|---|---|---|---|---|
| | 0.2 (mg/kg) | | 1 (mg/kg) | | 5 (mg/kg) | |
| Compound | lens | Sciatic nerve | lens | Sciatic nerve | lens | Sciatic nerve |
| 4,4'-imidazolidine]-2',5'-dione | | | | | | |
| 6,7-Dichloro-2-methyl-spiro-]chroman-4,4'-imidazolidine]2',5'-dione | — | — | — | — | 88 | — |
| 2-Methyl-spiro-[chroman-4,4'-imidazolidine]-2',5'-dione | — | — | — | — | 54 | 77 |

TABLE 2

| | Compound | Inhibition of sorbitol accumulation (%) | |
|---|---|---|---|
| | | lens | Sciatic nerve |
| Control compound | 6-Fluoro-spiro-[chroman-4,4'-imidazolidine]-2',5'-dione | 77 | 88 |
| | 6-Chloro-2,2-dimethyl-spiro-[chroman-4,4'-imidazolidine]-2',5'-dione | 89 | 100 |
| | 6-Fluoro-2,2-dimethyl-spiro-[chroman-4,4'-imidazolidine]-2',5'-dione | 81 | 93 |
| | 6,8-Dichloro-2,2-dimethyl-spiro-[chroman-4,4'-imidazolidine]-2',5'-dione | 87 | 55 |
| Compound according to this invention | 5-Chloro-2-methyl-spiro-[benzofuran-3,4'-imidazolidine]-2',5'-dione | 95 | 45 |
| | 6-Fluoro-2-methyl-spiro-[chroman-4,4'-imidazolidine]-2',5'-dione | 96 | 100 |
| | 6-Chloro-2-methyl-spiro-[chroman-4,4'-imidazolidine]-2',5'-dione | 97 | 82 |
| | 6-Bromo-2,2-dimethyl-spiro-[chroman-4,4'-imidazolidine]-2',5'-dione | 88 | 100 |

EXPERIMENT 2

The effect on cataract formation in glactosemic rats

Using four weeks old male Sprague-Dawley rats under feeding a diet containing 30% galactose, the control compound, 6-fluoro-spiro-[chroman-4,4'-imidazolidine]-2',5'-dione and the compound according to this invention, 6-chloro-2,2-dimethyl-spiro-[chroman-4,4'-imidazolidine]-2',5'-dione were orally administered once a day at dose levels of 1 mg/kg, 5 mg/kg and 25 mg/kg, respectively. On the 16th day of the study (24 hours after the final administration) lenticular opacities were observed, and then the lens and the sciatic nerve were enucleated to determine the content of carbohydrates.

RESULTS (1) Inhibition effect on cataract formation

The results are shown in FIG. 1 and Table 3.

FIG. 1 shows the inhibition effects of the control compound and the compound according to this invention on cataract formation in galactosemic rats. The abscissa in FIG. 1 indicates the number of days from the beginning of feeding of a 30% galactose diet, and the ordinate indicates the percentages of appearance of the cataract.

In FIG. 1, the following mark represents the cases, respectively:

⊙ : the galactose control where no compound is administered,
● : received the control compound at 1 mg/kg,
▲ : received the control compound at 5 mg/kg,
  : received the compound according to this invention at 1 mg/kg.

As shown apparently in FIG. 1, lenticular opacities were observed in galactose controls on the third day of the study while the delaying inhibitory effect on the appearance of the cataract was observed during the administration of the medicines. When the dose is over the range depicted in FIG. 1, i.e., 25 mg/kg for the control compound and 5 mg/kg, 25 mg/kg for the compound according to this invention, lenticular opacities were not observed even on the 16th day of the study.

Table 3 shows the results of the visual observation of lenticular opacities on the 16th day of the study. In Table 3, a symbol — represents the case of no opacity and +, ++, +++ show the grade of the opacity, respectively.

TABLE 3

| Compound | Dose (mg/kg) | | — | + | ++ | +++ | Total |
|---|---|---|---|---|---|---|---|
| Control | 0 | Right | | | | 6 | 6 |
| | | Left | | | | 6 | 6 |
| | 1 | Right | | | 2 | 4 | 6 |
| | | Left | | | 3 | 3 | 6 |
| Control compound | 5 | Right | 2 | 4 | | | 6 |
| | | Left | 2 | 4 | | | 6 |
| | 25 | Right | 6 | | | | 6 |
| | | Left | 6 | | | | 6 |
| | 1 | Right | 5 | 1 | | | 6 |
| Compound according to this invention | | Left | 5 | 1 | | | 6 |
| | 5 | Right | 6 | | | | 6 |
| | | Left | 6 | | | | 6 |
| | 25 | Right | 6 | | | | 6 |
| | | Left | 6 | | | | 6 |

It is apparent from FIG. 1 and Table 3 that the compound according to this invention is superior to the control compound.

(2) The Inhibition effect on the galactitol accumulation in the lens and the sciatic nerve Results are shown in Table 4.

TABLE 4

| Compound | Dose (mg/kg) | Inhibition of galactitol accumulation (%) | |
|---|---|---|---|
| | | lens | Sciatic nerve |
| Control compound | 1 | −11 | 1 |
| | 5 | 5 | −12 |
| | 25 | 22 | 17 |
| Compound according to this invention | 1 | 2 | 5 |
| | 5 | 19 | 50 |
| | 25 | 46 | 74 |

As shown apparently in Table 4, the compound according to this invention is remarkably superior to the control compound with respect to the inhibition of galactitol accumulation. Among others, the inhibitory effect of the compound of this invention on galactitol accumulation in the sciatic nerve is superior to that of the control compound to the extent of five times or more.

EXPERIMENT 3

Inhibition effect on aldose reductase

Aldose reductase was prepared by the method of Hayman et al. [S. Hayman and K.K. Kinoshita; Journal of Biological Chemistry, Vol. 240, p. 877 (1965)], and the inhibition activity on aldose reductase was determined by the method of Gabbay et al. [K. H. Gabbay and J. H. Kinoshita, Method in Enzymology, Vol. 41, p. 159 (1975)].

Table 5 shows the results. In Table 5, $ID_{50}$ represents the concentration of 50% inhibition on aldose reductase.

TABLE 5

| | Compound | Inhibition (%) | | | | $ID_{50}$ (M) |
|---|---|---|---|---|---|---|
| | | $10^{-7}$ (M) | $3 \times 10^{-7}$ (M) | $10^{-6}$ (M) | $3 \times 10^{-6}$ (M) | |
| Control compound | 6-Fluoro-spiro-[chroman-4,4'-imidazolidine]-2',5'-dione | 2 | 17 | 53 | 78 | $1 \times 10^{-6}$ |
| Compound according to this invention | 6-Chloro-2,2-dimethyl-spiro-[chroman-4,4'-imidazolidine]-2',5'-dione | −4 | 8 | 47 | 79 | $1 \times 10^{-6}$ |
| | 6-Fluoro-2,2-dimethyl-spiro-[chroman-4,4'-imidazolidine]-2',5'-dione | 0 | 12 | 40 | 70 | $2 \times 10^{-6}$ |
| | 6-Chloro-2-methyl-spiro-[chroman-4,4'-imidazolidine]-2',5'-dione | 0 | 31 | 84 | 92 | $4 \times 10^{-7}$ |
| | 6-Fluoro-2-methyl-spiro-[chroman-4,4'-imidazolidine]-2',5'-dione | 7 | 31 | 77 | 91 | $5 \times 10^{-7}$ |

When the compounds according to this invention are used as medicines for the treatment of and prevention of the various chronic symptoms accompanying diabetes mellitus, that is, the complications of diabetes mellitus, for example, diabetic cataracts, diabetic neuropathy, fine blood-vessel lesions such as the diabetic nephrosis and the like, diabetic retinopathy, and various ateriosclerotic blood-vessel lesions originating from diabetes mellitus, they are administered orally, parenterally or topically. Although the administration dosages of these compounds are varied depending on the symptones of diseases, the dosages of about 0.1 to about 300 mg, preferably about 0.1 to about 100 mg per day may generally be administered to an adult patient.

In case of formulating the compounds according to this invention, the compounds may be prepared in various types of formulations such as tablets, granules, powders, capsules, injections, suppositories and the like, by conventional methods employed in the technical field of formulation.

Namely, in case of the production of solid types of oral formulations, the formulation is prepared by adding to the subject active compound, excipients and, if necessary, binders, disintegrators, lubricants, colorants, taste and odor correctives, and casting into tablets, coated tablets, granules, powders, capsules and the like by a conventional manner.

Illustrative excipients which may be employed include lactose, corn starch, white sugar, glucose, sorbitol, crystalline cellulose and the like.

There may be mentioned, as binders, polyvinyl alcohol, polyvinyl ether, ethylcellulose, methylcellulose, gum arabic, tragacanth gum, gelatine shellac, hydroxypropyl cellulose, hydroxypropyl starch, polyvinyl pyrolidone, white sugar, sorbitol and the like.

Disintegrators include starch, agar-agar, gelatin powder, crystalline cellulose, calcium carbonate, sodium hydrogen carbonate, calcium succinate, dextrin, pectin and the like.

Illustrative lubricants include magnesium stearate, talc, polyethylene glycol, silica, hardening vegetable oils and the like.

There may be mentioned, as colorants materials which are acceptable to add to the medicine.

Taste and odor corrective include cocoa powder, menthol, aromatic powder, peppermint oil, borneol, cinnamon powder and the like.

These tablets and granules may be, of course, properly coated, if necessary, by way of sugar coating, gelatin coating and the like.

The following examples illustrate the preferred embodiments of this invention. They are not, however, intended in any way to limit the scope of this invention.

EXAMPLE 1

6-Fluoro-2-methyl-spiro-[chroman-4,4'-imidazolidine]-2',5'-dione (1) Synthesis of 6-fluoro-2-methyl-4-chromanone 11.2 G (0.1 mol) of para-fluorophenol and 17.2 g (0.2 mol) of crotonic acid were dissolved in 100 ml of polyphosphoric acid, and the solution was reacted with vigorously stirring at 120° C. for 8 hours. After cooling, the reaction solution was poured into 450 ml of iced 2N-sodium hydroxide solution, and the mixture was extracted with 500 ml of chloroform. The chloroform layer was washed with 2N-sodium hydroxide solution and with water, followed by drying over magnesium sulfate. The solvent was distilled off, and the residue was recrystallized from n-hexane in the amount of about ten times. There were thus obtained 5.8 g (yield: 32%) of the subject material, 6-fluoro-2-methyl-4-chromanone.

Melting point: 68°–69° C.

(2) Synthesis of 6-fluoro-2-methyl-spiro-[chroman-4,4'-imidazolidine]-2',5'-dione A 300 ml autoclave was charged with 10.8 g (0.06 mol) of 6-fluoro-2-methyl-4-chromanone produced by the process as described in the above paragraph (1), 120 g of acetamide, 11.7 g (0.18 mol) of potassium cyanide, and 37.4 g (0.39 mol) of ammonium carbonate. The contents were reacted with heating at 70° C. for 24 hours. After completion of the reaction, the reaction solution was dissolved in 600 ml of water and acidified with hydrochloric acid. The crystalline mass deposited was recovered by filtration, and dissolved in 600 ml of aqueous 2N-sodium hydroxide solution. Active carbon was added to the mixture. The active carbon was removed by filtration and the filtrate was acidified with hydrochloric acid. Crystalline materials deposted were removed by filtration, and washed with water, dried, then recrystallized from ethyl alcohol. There were thus obtained 5.8 g (yield: 39%) of the subject compound, 6-fluoro-2-methyl-spiro-[chroman-4,4'-imidazolidine]-2',5'-dione having the melting point and the elementary analysis as follows:

Melting point: 233°–235° C.

| Elementary analysis for $C_{12}H_{11}FN_2O_3$ | | | |
|---|---|---|---|
| | C | H | N |
| Calculated (%) | 57.60 | 4.43 | 11.20 |
| Found (%) | 57.53 | 4.44 | 11.21 |

Further, there was obtained from the mother liquor of recrystallization, a crystalline material having the melting point of 230°–232° C., which was one of the diastereomers of the subject compound.

The proportion of the previously described crystalline material to the latter crystalline material was 10:1. It has been found that, among the said diastereomers, the one which has the melting point of 233°–235° C. and is predominantly produced has higher activities in areas such as the inhibition of sorbitol accumulation by 3–5 times as compared with the other isomer which has the melting point of 230°–232° C.

Since the former crystalline 6-fluoro-2-methyl-spiro-[chromane-4,4'-imidazolidine]-2',5'-dione (melting point: 233°–235° C.) is dl-type product, the said product was subjected to optical resolution in accordance with the following procedure.

(1) An aqueous quinine methohydroxide solution was prepared from quinine, in accordance with the method as described in R. T. Major, J. Finkelstein, J. A. C. S., 63, 1368(1941). To 0.02 mol of the solution were added 120 ml of methanol solution containing 4.7 g (0.02 mol) of dl-6-fluoro-2-methyl-spiro-[chromane-4,4'-imidazolidine[-2',5'-dione. The resulting mixture was dried under reduced. The residue was dissolved in 100 ml of ethanol. The solution was concentrated to the volume of 35 ml, and the concentrated solution was allowed to stand. The crystalline mass deposited out was recovered by filtration, and was once more recrystallized from ethanol. There were thus obtained 2.4 g of crystalline N-methyl-quinium d-6-fluoro-2-methyl-spiro-[chromane-4,4'-imidazolidine]-2',5'-dione salt.

Melting point: 216°–217° C.

$[\alpha]_D^{20} = +37.6°$

| Elementary analysis for $C_{12}H_{10}FN_2O_3$ | | | |
|---|---|---|---|
| | C | H | N |
| Calculated (%) | 67.33 | 6.34 | 9.52 |
| Found (%) | 67.20 | 6.40 | 9.45 |

(2) 1.5 g of the above salt were dissolved in 200 ml of ethanol, to which solution were added 5 ml of a concentrated hydrochloric acid. To the solution were added 100 ml of water, to deposit out the crystalline mass, which was in turn recovered by filtration. The mass was subjected to the recrystallization from an aqueous alcohol solution to obtain 0.4 g of colorless Pillow d-6-fluoro-2-methyl-spiro-[chromane-4,4'-imidazolidine]-2',5'-dione.

Melting point: 250°–251° C.

$[\alpha]_D^{20} = +226.3°$ (in methanol)

| Elementary analysis for $C_{12}H_{11}FN_2O_3$ | | | |
|---|---|---|---|
| | C | H | N |
| Calculated (%) | 57.60 | 4.43 | 11.20 |
| Found (%) | 57.48 | 4.42 | 11.02 |

(3) As to the mother liquor which remained from the filtration of the primary of predominant crystalline mass of N-methyl-quinium.d-6-fluoro-2-methyl-spiro-[chromane-4,4'-imidazolidine]-2',5'-dione salt, the liquor was concentrated to obtain N-methyl-quinium.l-6-fluoro-2-methyl-spiro-[chromane-4,4'-imidazolidine]-2',5'-dione salt which was a viscous yellowish oil substance. Alcohol was added to the substance to form an alcohol solution, to which was then added concentrated hydrochloric acid. The crystalline mass deposited out was recovered by filtration. The mass was recrystallized from an aqueous alcohol solution to obtain 0.3 g of l-6-fluoro-2-methyl-spiro-[chromane-4,4'-imidazolidine]-2',5'-dione.

Melting point: 244°–245° C.

$[\alpha]_D^{20} = -189.7°$ (in alcohol)

| Elementary analysis for $C_{12}H_{11}FN_2O_3$ | | | |
|---|---|---|---|
| | C | H | N |
| Calculated (%) | 57.60 | 4.43 | 11.20 |
| Found (%) | 57.36 | 4.42 | 11.03 |

The activity of the aforementioned d-6-fluoro-2-methyl-spiro-[chromane-4,4'-imidazolidine]-2',5'-dione is about twice that of the corresponding dl-type product. More particularly, by the determination of inhibition effect on the Aldose reductase in a similar manner as describing in Experiment 3, $ID_{50}$ of the d-type product was $9.3 \times 10^{-8}$, whereas $ID_{50}$ of the dl-type product was $1.8 \times 10^{-7}$.

EXAMPLE 2

6-Chloro-2-methyl-spiro-[chroman-4,4'-imidazolidine]-2',5'-dione (1) Synthesis of 6-chloro-2-methyl-4-chromanone By the same procedure as described in the paragraph (1) of Example 1, the subject compound, 6-chloro-2-methyl-4-chromanone in amount of 5.8 g (yield: 30.0%) was obtained.
Melting point: 100°–102° C.

(2) Synthesis of 6-chloro-2-methyl-spiro-[chroman-4,4'-imidazolidine]-2',5'-dione Using the 6-chloro-2-methyl-4-chromanone produced by the process as described in the above paragraph (1), there were obtained, by the same procedure as described in the paragraph (2) of Example 1, the subject compound, 6-chloro-2-methyl-spiro-[chroman-4,4'-imidazolidine]-2',5'-dione in amount of 8.8 g (yield: 55%) having the following melting point and elementary analysis:
Melting point: 283°–285° C.

| Elementary analysis for $C_{12}H_{11}ClN_2O_3$ | | | |
|---|---|---|---|
| | C | H | N |
| Calculated (%) | 54.05 | 4.16 | 10.50 |
| Found (%) | 54.10 | 3.71 | 10.55 |

Further, a crystallized material having melting point of 223°–228° C., which is one of the diastereomers of the subject compound was obtained from the mother liquor of recrystallization.

The proportion of the crystalline material previously described in the latter crystalline material was 8:1. It has been found that, among these diastereomers, the crystalline material predominantly produced, which has the melting point of 283°–285° C. has higher activities such as the inhibition of sorbitol accumulation by 3–5 times compared with the other material which has melting point of 223°–228° C.

SInce the former crystalline 6-chloro-2,2-dimethyl-spiro-[chromane-4,4'-imidazolidine]-2',5'-dione (melting point: 283°–285° C.) is a dl-type product, the said product was subjected to the optical resolution in accordance with the following procedure.

(1) 12.3 g (0.046 mol) of the above-obtained dl-6-chloro-2-methyl-spiro-[chromane-4,4'-imidazolidine]-2',5'-dione were dissolved in 100 ml of methanol and 150 ml of acetone.

Apart from the above, an aqueous cinchonine-methohydroxide solution was prepared in accordance with the method as described in R. J. Major, J. Finkelstein, J. A. C. S. 63, 1368 (1941).

0.046 mol of the aqueous cinchonium-methohydroxide solution were added to the dl-6-chloro-2-methyl-spiro-[chromane-4,4'-imidazolidine]-2',5'-dione to precisely neutralize the latter. The mixed solution was concentrated under reduced pressure. To the resulting matter was added ethyl alcohol, followed by concentrating under reduced pressure. By repeating the above procedure, there was obtained an amorphous substance in the form of the N-methyl cinchonium salt.

The amorphous substance was dissolved in 120 ml of acetone. The solution was allowed to stand in a refrigerator, to provide a crystalline mass having $[\alpha]_D^{20} = +15.35°$ (c=0.267 EtOH). The crystalline mass was recrystallized several times from acetone to obtain 9 g of N-methylcinchonium salt of l-6-chloro-2-methyl-spiro-[chromane-4,4'-imidazolidine]-2',5'-dione.
Melting point: 171°–173° C.

$[\alpha]_D^{20} = +4.2°$ (c=0.297 EtOH)

| Elementary analysis for $C_{12}H_{10}ClN_2O_3 \cdot C_{20}H_{25}N_2O$ | | | |
|---|---|---|---|
| | C | H | N |
| Calculated (%) | 66.77 | 6.12 | 9.73 |
| Found (%) | 66.34 | 6.39 | 9.51 |

(2) The above-mentioned salt was treated with 200 ml of ethyl acetate and 300 ml of 1N hydrochloric acid. The resulting organic layer was washed with water, dried over magnesium sulphate, followed by filtration. The filtrate was concentrated under a reduced pressure to obtain 4 g of the crude product, which was then recrystallized from 130 ml of ethyl acetate to provide 2.5 g (yield: 40.6%) of l-6-chloro-2-methyl-spiro-[chromane-4,4'-imidazolidine]-2',5'-dione.
Melting point: 284°–285° C.

$[\alpha]_D^{20} = -213.4°$ (c=0.097 EtOH)

| Elementary analysis for $C_{12}H_{11}ClN_2O_3$ | | | |
|---|---|---|---|
| | C | H | N |
| Calculated (%) | 54.02 | 4.15 | 10.50 |
| Found (%) | 54.01 | 4.11 | 10.51 |

(3) The above-mentioned l-spiro-hydantoin salt was recovered by filtration to leave the mother liquor, which was in turn concentrated to give 10.5 g of the crude product having $[\alpha]_D^{20} = +260.6$ (c=0.267 EtOH). The crude product was recrystallized several times from acetone to obtain 6.5 g of N-methyl-cinchonium salt of d-6-chloro-2-methyl-spiro-[chromane-4,4'-imidalidine]-2',5'-dione.
Melting point: 223.5°–225° C.

$[\alpha]_D^{20} = +264.2$ (c=0.334 EtOH)

| Elementary analysis for $C_{12}H_{10}ClN_2O_3 \cdot C_{20}H_{25}N_2O$ | | | |
|---|---|---|---|
| | C | H | N |
| Calculated (%) | 66.77 | 6.12 | 9.73 |
| Found (%) | 66.98 | 6.28 | 9.71 |

(4) 5 g of the above product were treated with 500 ml of ethyl acetate and 200 ml of 1N hydrochloric acid. The resulting organic layer was washed with water, dried over magnesium sulphate, followed by filtration. The filtrate was concentrated under a reduced pressure to obtain 2.2 g of a crude crystalline mass, which was then recrystallized from 70 ml of ethyl acetate to provide 1.47 g (yield: 27.4%) of d-6-chloro-2-methyl-spiro-[chromane-4,4'-imidazolidine]-2',5'-dione.
Melting point: 285°–287° C.

$[\alpha]_D^{20} = +219.5°$ (c=0.205 EtOH)

| Elementary analysis for $C_{12}H_{11}ClN_2O_3$ | | | |
|---|---|---|---|
| | C | H | N |
| Calculated (%) | 54.02 | 4.15 | 10.50 |

| Elementary analysis for $C_{12}H_{11}ClN_2O_3$ | | | |
|---|---|---|---|
| | C | H | N |
| Found (%) | 54.12 | 4.15 | 10.51 |

The activity of the aforementioned d-6-chloro-2-methyl-spiro-[chromane-4,4'-imidazolidine]-2',5'-dione is about twice as compared with that of the corresponding dl-type product. More particularly, by the determination of inhibitory effect on the Aldose reductase in a similar manner as described in the Experiment 3, the ID50 of the d-type prodcut was found to be $4.3 \times 10^{-8}$, whereas $ID_{50}$ of the dl-type product was found to be $7.7 \times 10^{-8}$.

EXAMPLE 3

6-Chloro-2,2-dimethyl-spiro-[chroman-4,4'-imidazolidine]-2',5'-dione (1) Synthesis of 6-chloro-2,2-dimethyl-4-chromanone A 200 ml 4-necked flask was charged with 34.6 g (0.203 mol) of 5-chloro-2-hydroxyacetophenone and 15.5 g (0.258 mol) of acetone. The mixture was dissolved in 60 ml of benzene, and 4.1 g (0.0577 mol) of pyrrolidine were added dropwise thereto. After stirring for one hour, a condenser provided with water separator was mounted on the flask, and the solution was refluxed. Thereafter, additional 8–12 ml of acetone were added, and the reflux was continued for additional 3 hours. When the reaction was completed, the reaction mixture was washed three times with 150 ml of 2N-NaOH solution and with water. The mixture was washed again three times with 2N-NaOH solution and with water, then dried over MgSO4. The solvent was distilled off and the residue was distilled in vacuo. Thus, 26.8 g (yield: 62.6%) of the subject compound, 6-chloro-2,2-dimethyl-4-chromanone was obtained.

Boiling point: 95°–100° C./0.2–0.3 mmHg.

(2) Synthesis of 6-chloro-2,2-dimethyl-spiro-[chroman-4,4'-imidazolidine]-2',5'-dione A 300 ml autoclave was charged with 10 g (0.0474 mol) of 6-chloro-2,2-dimethyl-4-chromanone produced by the process described in the above paragraph (1), 9.6 g (0.148 mol) of potassium cyanide (KCN), 30 g (0.313 mol) of ammonium carbonate[(NH4)2CO3] and 190 g of acetamide. The contents were heated at 70° C. for 24 hours and then at 110° C. for 24 hours. After cooling, the mixture was dissolved in 950 ml of water, and the solution was acidified with concentrated hydrochloric acid. The crystalline materials deposited were recovered by filtration, and dissolved in 400 ml of aqueous 2N-NaOH solution. The solution was filtered. The filtrate was acidified with concentrated hydrochloric acid and allowed to stand overnight. Crystalline material deposited was recovered by filtration, dried, and recrystallized from ethyl alcohol, to obtain 8.3 g (yield: 61%) of the subject compound, 6-chloro-2,2-dimethyl-spiro-[chroman-4,4'-imidazolidine]-2',5'-dione.

Melting point: 281°–283° C.

| Elementary analysis: $C_{13}H_{13}ClN_2O_3$ | | | |
|---|---|---|---|
| | C | H | N |
| Calculated (%) | 55.60 | 4.66 | 9.77 |

| Elementary analysis: $C_{13}H_{13}ClN_2O_3$ | | | |
|---|---|---|---|
| | C | H | N |
| Found (%) | 55.72 | 4.78 | 10.17 |

EXAMPLE 4

Cyclohexane<spiro-2>-6-methyl-spiro-[chroman-4,4'-imidazoline]-2',5'-dione (1) Synthesis of cyclohexane<spiro-2>-4-chromanone A 4-necked round bottom flask equipped with a water separator was charged with 8 g (0.06 mol) of 2-hydroxy-5-methylacetophenone, 7.65 (0.078 mol) of cyclohexanone and 15 ml of toluene. 1.2 g (0.017 mol) of pyrrolidine were added thereto dropwise at the room temperature. After stirring for 30 minutes to one hour, the mixture was refluxed for 13 hours. After the completion of the reaction, the reaction mixture was cooled and washed with 200 ml of 2N-NaOH solution and with water. The mixture was then washed with 2N-HCl solution and with water, subsequently dried over MgSO4 and treated with an active carbon. The mixture was filtered and the solvent was distilled off, to obtain 7.7 g (yield: 55.8%) of the subject compound, cyclohexane<spiro-2>-4-chromanone.

(2) Synthesis of cyclohexane<spiro-2>-6-methyl-spiro-[chroman-4,4'-imidazolidine]-2',5'-dione A 100 ml autoclave was charged with 4.6 g (0.02 mol) of cyclohexane<spiro-2>-4-chromanone produced by the process described in the above paragraph (1), 4 g (0.06 mol) of potassium cyanide (KCN), 12.6 g (0.13 mol) of ammonium carbonate [(HN4)2CO3] and 80 g of acetamide (CH3CONH2). The mixture was reacted at 60° C. for 24 hours, and then at 110° C. for 24 hours. After cooling, the reaction mixture was dissolved in 400 ml of water, the acidified with concentrated hydrochloric acid. The crystalline material deposited was recovered by filtration. The crystalline material was again dissolved in 200 mol of 2N-NaOH solution. The solution was filtered, and the filtrate was acidified with concentrated hydrochloric acid. The crystalline material deposited was recovered by filtration and dried. The material was recrystallized from ethanol, to obtain 1.8 g (yield: 30%) of the subject compound, cyclohexane<spiro-2>-6-methyl-spiro-[chroman-4,4'-imidazolidine].

Melting point: 267°–269° C.

| Elementary analysis for $C_{17}H_{20}N_2O_3$ | | | |
|---|---|---|---|
| | C | H | N |
| Calculated (%) | 67.97 | 6.71 | 9.32 |
| Found (%) | 67.25 | 6.97 | 8.77 |

EXAMPLE 5

5-Chloro-2,2-dimethyl-spiro-[benzofuran-3,4'-imidazolidine]-2',5'-dione (1) Synthesis of 5-chloro-2,2-dimethyl-3-benzofuranone With stirring under ice-cooling, 3 g of metallic sodium were added in 100 ml of absolute ethanol to dissolve the metal. Then, 12.5 g (0.045 mol) of 4-chloro-2-(2-bromoisobutyryl)phenol dissolved in 60 ml of benzene was added to the said solution dropwise for about 15 minutes under heating to reflux (internal temperature: 80° C.). After the completion of the dropping, the stirring was continued for additional 30–60 minutes with heating and the solution was vacuum-concentrated to one third in volume. The solution concentrated was diluted with large amount of water, and the solution was extracted with ether. The ether layer was washed with water, then vacuum-concentrated to dryness to produce 10 g of crude crystallized subject compound, 5-chloro-2,2-dimethyl-4-benzofuran. Then, the crude product was recrystallized from methanol, to obtain 7.3 g (yield: 82.5%) of the subject compound in colorless pillow crystal.

Melting point: 73.5°–74.5° C.

(2) Synthesis of 5-chloro-2,2-dimethyl-spiro-[benzofuran-3,4'-imidazolidine]-2',5'-dione A mixture comprising 6.9 g (0.035 mol) of 5-chloro-2,2-dimethyl-3-benzofuran produced by the process of the above paragraph (1), 7.0 g (0.107 mol) of potassium cyanide (KCN), 20 g (0.21 mol) of ammonium carbonate [(NH$_4$)$_2$CO$_3$] and 70 g of acetamide was reacted on an oil bath at 85°–95° C. for 20 hours, and then at 105°–110° C. for 9 hours. The reaction mixture was poured into iced water to dissolve therein. The solution was acidified with hydrochloric acid, and stirred for about 3 hours. The crystalline materials deposited were recovered by filtration. The filtrate was extracted with ethyl acetate. The crystalline materials deposited were combined with the ethyl acetate layer. The whole was heated to reflux. Materials insoluble in ethyl acetate were removed by filtration. The ethyl acetate solution was concentrated, and crystalline material despited was recrystallized from methanol, to obtain 5.63 g (yield: 60.3%) of the subject compound, 5-chloro-2,2-dimethyl-spiro-]benzofuran-3,4'-imidazolidine]-2',5'-dione.

Melting point: 228.5°–229° C.

| Elementary analysis: C$_{12}$C$_{11}$ClN$_2$O$_3$ | | | |
|---|---|---|---|
| | C | H | N |
| Calculated (%) | 54.04 | 4.16 | 10.50 |
| Found (%) | 54.14 | 4.05 | 10.52 |

EXAMPLES 6–30

In the same manner as described in the Examples 1–5, there were obtained the compounds as listed in Table 6.

In Table 6, the positions of the substituents X$_1$ and X$_2$ shown in the structural formula differ from each other in the n=0 or 1 and said positions are indicated on the basis of the number as shown in the following:

(i) the case of n = 0

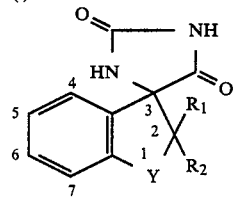

(ii) the case of n = 1

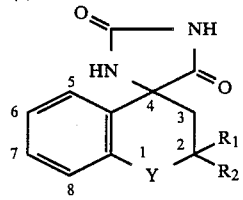

The rings of cyclohexane and cyclopentane shown in Examples 21–24 in Table 6 indicate that the spiro bond is formed on the position 2 of the respective structural formulae as shown above.

TABLE 6

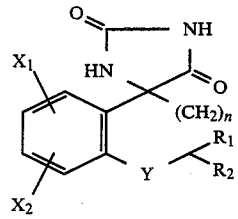

| Ex. | X$_1$ | X$_2$ | R$_1$ | R$_2$ | Y | n | Melting Point (°C.) | Molecular Formula | Elementary Analysis (%) Upper row: Calculated Lower row: Found | | |
|---|---|---|---|---|---|---|---|---|---|---|---|
| | | | | | | | | | C | H | N |
| 6 | 6-F | H | —CH$_3$ | —CH$_3$ | O | 1 | 293–294 | C$_{13}$H$_{13}$N$_2$O$_3$F | 59.08 | 4.95 | 10.60 |
| | | | | | | | | | 59.08 | 4.96 | 10.65 |
| 7 | 6-CH$_3$ | H | —CH$_3$ | —CH$_3$ | O | 1 | 247–249 | C$_{14}$H$_{16}$N$_2$O$_3$ | 64.59 | 6.19 | 10.76 |
| | | | | | | | | | 64.21 | 6.33 | 10.92 |
| 8 | 6-OCH$_3$ | H | —CH$_3$ | —CH$_3$ | O | 1 | 186–188 | C$_{14}$H$_{16}$N$_2$O$_4$ | 60.85 | 5.83 | 10.14 |
| | | | | | | | | | 61.33 | 5.99 | 10.30 |
| 9 | 6-Cl | 8-Cl | —CH$_3$ | —CH$_3$ | O | 1 | 244–245 | C$_{13}$H$_{12}$N$_2$O$_3$Cl$_2$ | 49.51 | 3.83 | 8.88 |
| | | | | | | | | | 49.86 | 4.07 | 8.45 |
| 10 | 6-Br | H | —CH$_3$ | —CH$_3$ | O | 1 | 299–300 | C$_{13}$H$_{13}$O$_3$N$_2$Br | 48.01 | 4.03 | 8.62 |
| | | | | | | | | | 47.96 | 4.03 | 8.57 |
| 11 | 6-F | H | —C$_2$H$_5$ | —C$_2$H$_5$ | O | 1 | 201–204 | C$_{15}$H$_{17}$N$_2$O$_3$F | 61.63 | 5.86 | 9.59 |
| | | | | | | | | | 61.68 | 5.89 | 9.56 |
| 12 | 6-Cl | H | —C$_2$H$_5$ | H | O | 1 | 267–268 | C$_{13}$H$_{13}$N$_2$O$_3$Cl | 55.60 | 4.66 | 9.97 |
| | | | | | | | | | 56.05 | 4.67 | 10.04 |
| 13 | 6-Cl | H | —n-C$_3$H$_7$ | H | O | 1 | 249–251 | C$_{14}$H$_{15}$N$_2$O$_3$Cl | 57.03 | 5.12 | 9.50 |
| | | | | | | | | | 57.06 | 4.87 | 9.49 |

TABLE 6-continued

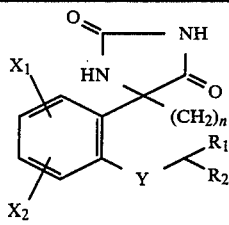

| Ex. | X₁ | X₂ | R₁ | R₂ | Y | n | Melting Point (°C.) | Molecular Formula | C (Calc/Found) | H (Calc/Found) | N (Calc/Found) |
|---|---|---|---|---|---|---|---|---|---|---|---|
| 14 | 6-Cl | H | —CH(CH₃)CH₃ | H | O | 1 | 247–249 | $C_{14}H_{15}N_2O_3Cl$ | 57.03 / 56.49 | 5.12 / 4.96 | 9.50 / 9.47 |
| 15 | 6-Cl | H | —n-$C_4H_9$ | H | O | 1 | 247–248 | $C_{15}H_{17}N_2O_3Cl$ | 58.33 / 58.38 | 5.54 / 5.53 | 9.07 / 9.17 |
| 16 | 6-Cl | H | —CH₃ | H | O | 1 | 293–294 | $C_{12}H_9ClN_2O_3$ | 54.05 / 54.10 | 4.16 / 3.71 | 10.50 / 10.55 |
| 17 | 6-OCH₃ | H | —CH₃ | H | O | 1 | 225–227 | $C_{13}H_{14}N_2O_4$ | 59.54 / 59.22 | 5.38 / 5.15 | 10.68 / 10.74 |
| 18 | 7-Cl | H | —CH₃ | H | O | 1 | 254–255 | $C_{12}H_{11}ClN_2O_3$ | 54.05 / 53.98 | 4.16 / 4.15 | 10.50 / 10.44 |
| 19 | 6-CH₃ | H | —CH₃ | H | O | 1 | 265–267 | $C_{13}H_{14}N_2O_3$ | 63.40 / 63.19 | 5.73 / 5.57 | 11.38 / 11.22 |
| 20 | 6-Cl | 7-Cl | —CH₃ | H | O | 1 | 296–297 | $C_{12}H_{10}Cl_2N_2O_3$ | 52.01 / 51.88 | 3.64 / 3.75 | 10.11 / 10.01 |
| 21 | 6-Cl | H | cyclopentyl | | O | 1 | 263–265 | $C_{15}H_{15}N_2O_3Cl$ | 58.71 / 58.84 | 4.92 / 4.76 | 9.13 / 9.40 |
| 22 | 6-Cl | H | cyclohexyl | | O | 1 | 241–243 | $C_{16}H_{17}N_2O_3Cl$ | 59.88 / 59.78 | 5.34 / 5.43 | 8.73 / 8.86 |
| 23 | 6-OCH₃ | H | cyclopentyl | | O | 1 | 250–252 | $C_{16}H_{18}N_2O_4$ | 63.56 / 63.68 | 6.00 / 6.32 | 9.27 / 9.21 |
| 24 | 6-CH₃ | H | cyclopentyl | | O | 1 | 257–259 | $C_{16}H_{18}N_2O_3$ | 67.11 / 66.96 | 6.33 / 6.46 | 9.78 / 9.17 |
| 25 | H | H | —CH₃ | —CH₃ | O | 1 | 249–250 | $C_{13}H_{14}N_2O_3$ | 63.39 / 63.74 | 5.73 / 5.83 | 11.37 / 11.43 |
| 26 | H | H | —CH₃ | H | O | 1 | 255–259 | $C_{12}H_{12}N_2O_3$ | 62.06 / 62.22 | 5.21 / 5.27 | 12.06 / 11.85 |
| 27 | H | H | —CH₃ | —CH₃ | S | 1 | 258–260 | $C_{13}H_{14}O_2N_2S$ | 59.53 / 59.91 | 5.38 / 5.27 | 10.68 / 10.79 |
| 28 | 6-Cl | H | phenyl | H | O | 1 | 299–300 | $C_{17}H_{13}N_2O_3Cl$ | 62.10 / 62.20 | 3.98 / 3.75 | 8.52 / 8.63 |
| 29 | 5-Cl | H | —CH₃ | H | O | 0 | 239–242 | $C_{11}H_9O_3N_2Cl$ | 52.29 / 52.64 | 3.60 / 3.56 | 11.09 / 11.08 |
| 30 | 6-Cl | H | —CH₃ | H | S | 1 | 278–279 | $C_{12}H_{11}O_2N_2ClS$ | 50.97 / 50.91 | 3.92 / 3.95 | 9.90 / 9.92 |

What is claimed is:
1. the hydantoin derivative 6-fluoro-2,2-dimethyl-spiro-[chroman-4,4'-imidazolidine]-2',5'-dione and pharmaceutically acceptable salts thereof.

* * * * *